United States Patent [19]

Delbard

[11] Plant 4,440

[45] Jul. 17, 1979

[54] ROSE PLANT—ETERNA

[75] Inventor: Georges A. Delbard, Paris, France

[73] Assignee: Jackson & Perkins Co., Medford, Oreg.

[21] Appl. No.: 859,995

[22] Filed: Dec. 12, 1977

[51] Int. Cl.[2] ..... A01H 5/00

[52] U.S. Cl. ..... Plt./18

[58] Field of Search ..... Plt./18

*Primary Examiner*—Robert E. Bagwill

*Attorney, Agent, or Firm*—Klarquist, Sparkman, Campbell, Leigh, Hall & Whinston

[57] ABSTRACT

A vigorous, upright, well-branched rose plant of the hybrid tea class, with heavy, straight stems, having a unique clear color of Wilson's French Rose, with very little fragrance.

7 Drawing Figures

The present invention relates to a new and distinct cultivar of rose plant of the hybrid tea class which was originated by me by crossing the cultivars (Michele Meilland × Carla) × (Dr. Schweitzer × Super Star) with pollen of the cultivars (Queen Elizabeth × Provence).

The primary objective of this breeding was to produce a cultivar of the hybrid tea class, with a light clear pink flower color, suitable primarily for use in a greenhouse for the production of cut blooms. This objective was substantially achieved along with other desirable improvements as evidenced by the following unique combination of characteristics which are outstanding in this new cultivar and which distinguish it from its parents as well as from all other cultivars of which I am aware:

1. A vigorous, upright, well-branched plant of the hybrid tea class.
2. Heavy, straight stems.
3. A distinctive, unique, clear color of Wilson's French Rose, which changes very little from bud to a flower four days old.
4. Very little fragrance.

Asexual reproduction of this new cultivar by budding as performed at Evry, France and at Wasco, Calif., shows that the foregoing characteristics and distinctions come true to form and are established and transmitted through succeeding propagations.

The accompanying illustration shows typical specimens of the vegetative growth and flowers of this new cultivar in different stages of development, depicted in color as nearly true as it is reasonably possible to make the same in a color illustration of this character.

The following is a detailed description of my new rose cultivar with color in terminology in accordance with Wilson's Horticultural Color Chart except where ordinary dictionary significance of color is indicated.

Parentage:

*Seed parent.*—(Michele Meilland × Carla) × (Dr. Schweitzer × Super Star).

*Pollen parent.*—Queen Elizabeth × Provence

Classification:

*Botanical.*—Rosa hybrid.

*Commercial.*—Hybrid tea.

FLOWER

Observations made from specimens grown outside at Irvine, Calif., in August of 1977.

Blooming Habit: Continuous.

Bud:

*Size.*—¾" to 1" when petals start to unfurl.

*Form.*—Short, pointed.

*Color.*—When sepals first divide, Mottled Rhodonite Red (0022); when half blown, upper side of petals French Rose (520/1); lower side of petals French Rose (520/2).

*Sepals.*—Color: Outer surface Spinach Green (0960/1) overlaid with Garnet Brown (00918/3); inner surface Spinach Green (0960/1); three appendaged sepals lightly appendaged; two unappendaged sepals, hairy edged.

*Receptacle.*—Color: Spinach Green (0960/1) overlaid with Garnet Brown (00918/3). Shape: Funnel. Size: Large. Surface: Smooth.

*Peduncle.*—Length: Medium. Surface: Slightly prickly. Color: Medium green, bronzy on some. Strength: Stiff, erect, heavy.

*Opening.*—Slight recurving of outer petals, generally in spiral fashion.

Bloom:

*Size.*—Medium. Average open size 4" to 5".

*Borne.*—Mostly singly.

*Stems.*—Long.

*Form.*—When first open, high centered. Permanence: Retains its form to the end.

*Petalage.*—Number of petals under normal conditions: 35.

*Color.*—Center of flower: Upper side of petals between RHS 49D and French Rose (520/3). Reverse side of petals slightly lighter than a shade between RHS 49D and French Rose (520/3). Base of petals: A small indistinct area of Straw Yellow (604/2). General tonality from a distance: French Rose (520/2).

*Variegations.*—None.

*Discoloration.*—General tonality at end of first day, no change; third day, very little fading. Shows weather spotting when blooms remain on plant outside.

*Fragrance.*—Very little.

Petals:

*Texture.*—Thick.

*Shape.*—Broad, oval.

*Form.*—Tips slightly recurved.

*Arrangement.*—Imbricated. Petaloids in center, few.

*Persistence.*—Drop off cleanly.

*Lastingness.*—On the plant, very long. As cut flower, very long.

Reproductive Parts:

*Stamens, anthers.*—Medium. Color, yellow. Arrangement, regular around styles.

*Filaments.*—Color: French Rose (520).

*Pollen.*—Lemon yellow.

*Styles.*—Color: Mimosa Yellow (602) to Geranium Lake (20) near stigmas.

*Stigmas.*—Color: Straw Yellow (604/3).

PLANT

Form: Bush.

Growth: Very vigorous, upright, branching.

Foliage: Number of leaflets on normal mid-stem leaves: 5.

*Size.*—Medium.

*Quantity.*—Normal.

*Color.*—New foliage: Near Garnet Brown (00918/3). Old foliage: Parsley Green (00962).

Leaflets:

*Shape.*—Oval pointed.

*Texture.*—Leathery.

*Edge.*—Serrated.

*Serrations.*—Single.

*Petiole.*—Rachis: Color, reddish. Underside: Prickles.

*Stipules.*—Long, bearded.

*Disease resistance.*—Normally resistant to mildew under normal growing conditions at Irvine, Calif.

Wood:

*New wood.*—Color: Reddish. Bark: Smooth.

*Old wood.*—Color: Green. Bark: Smooth.

Prickles:

*Quantity.*—On main stalks from base, many. On laterals from stalk, ordinary.

*Form.*—Broad base, long, straight.

*Color when young.*—Brown.

*Position.*—Irregular.

Small prickles:

*Quantity.*—On main stalks, few. On laterals, few.

*Color.*—Brown.

I claim:

1. A new and distinct cultivar of rose of the hybrid tea class, substantially as herein shown and described, characterized particularly as to novelty by the unique combination of its uniform color of French Rose from bud to well-developed open flower; its vigorous plant, straight and relatively heavy stems.

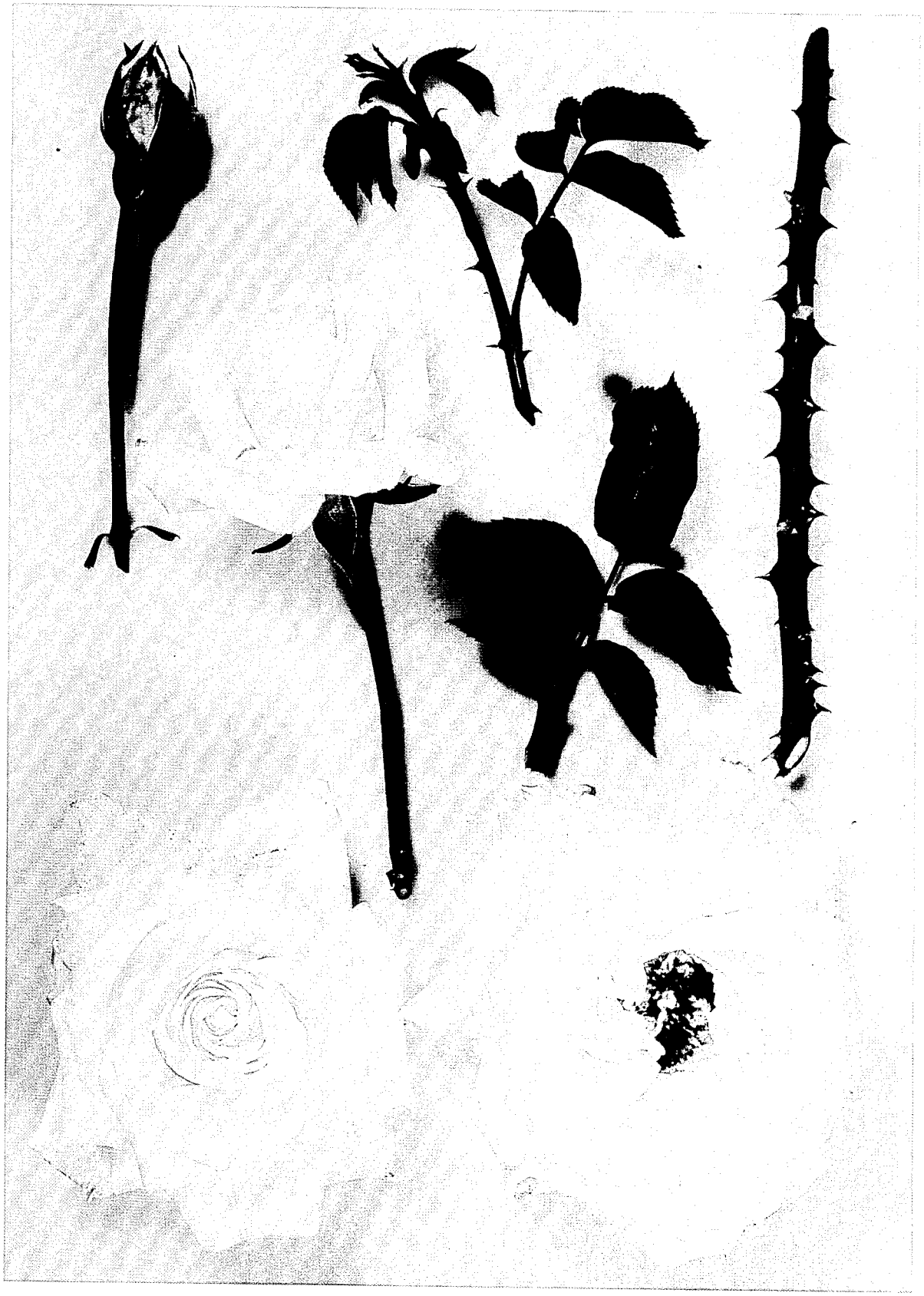

* * * * *